United States Patent [19]
Saltzman

[11] Patent Number: 4,777,961
[45] Date of Patent: Oct. 18, 1988

[54] HIGH SENSITIVITY STETHOSCOPIC SYSTEM AND METHOD

[76] Inventor: Bruce Saltzman, 7860 SW. 147th St., Miami, Fla. 33158

[21] Appl. No.: 787,635

[22] Filed: Oct. 15, 1985

[51] Int. Cl.$^4$ .............................................. A61B 5/02
[52] U.S. Cl. ................................... 128/715; 128/773; 128/963
[58] Field of Search .............. 128/643, 687, 695, 715, 128/773, 903; 181/126, 131; 381/67

[56] References Cited

U.S. PATENT DOCUMENTS

| | | | |
|---|---|---|---|
| 3,160,708 | 12/1964 | Andries et al. | 128/715 |
| 3,867,925 | 2/1975 | Ersek | 128/715 |
| 3,921,621 | 11/1975 | Baessler | 128/903 |
| 3,958,564 | 5/1976 | Langguth | 128/643 |
| 4,248,241 | 2/1981 | Tacchi | 128/715 |

FOREIGN PATENT DOCUMENTS 2152808  4/1973  Fed. Rep. of Germany ...... 128/643

Primary Examiner—William E. Kamm
Attorney, Agent, or Firm—McCormick, Paulding & Huber

[57] ABSTRACT

A lightweight, improved precordial suction stethescope constant monitoring system including a heart and breath sound detection means, solely mounted to patient using only suction or other connection means, and an inexpensive radio wave transmission means and a remote radio wave receiver and audio means. A quick connect suction cup or other stethoscope, which is especially suitable for use on the wet skin of a newborn, is used to provide the acoustical recess of the stethescope head. A microphone transducer located in the stethescope head or in a detachable housing is used for converting acoustical vibrations into an electrical impulse. The said remote radio wave receiving means amplifies and converts the electronically transmitted physiological condition information into an audible signal. This system allows the attending medical personnel to be totally free of any physical connection to the patient being monitored.

7 Claims, 4 Drawing Sheets

HIGH SENSITIVITY STETHOSCOPIC SYSTEM AND METHOD

BACKGROUND OF THE INVENTION

This invention relates to a solely patient mounted and supported constant monitoring suction stethoscopic and radio transmitter system and remote radio receiver and speaker. This system allows the attending professional anesthesiologist and staff members to be totally free of any physical connection to a particular patient or to the stethoscope supported by and connected to the chest of the patient except by radio waves transmitted from said radio transmitter to the remote radio receiver.

Today when an infant is born the only way to monitor cardiorespiratory function is to hold a stethoscope on the infant's chest or feel the pulsations of the umbilical cord. The only person who knows the results of these tests is the person listening with the stethoscope or holding the cord. Unfortunately, resuscitating a newborn requires the nurse or physician doing the resuscitation to use both hands to suction the infant, help it breathe and do other things necessary for resuscitation, so they cannot directly observe the cardiorespiratory status. An EKG could be attached to the infant and its sounds monitored by distant observers, but it tells nothing of therespiratory status of the infant.

In the past, such as described in U.S. Pat. No. 3,517,664, devices for monitoring blood pressure, pulse and respiration during anesthesia, having a two-way valve in which the passage from a blood pressure acoustic pickup to the earpiece is always open, but a pressure activated valve closes off the passage from a chestpiece to the earpiece automatically in response to inflation of the blood pressure cuff have been proposed. Such devices, connect the anesthesiologist physically to the patient, limiting his usefulness and freedom to attend to other duties. The anesthesiologist needs to be free to move in order to best serve the patient. This is especially true after the birth of a child when the anesthesiologist has two patients to attend.

The disclosure in U.S. Pat. No. 3,513,832 relates to a monitoring apparatus comprising a thermistor probe for insertion into the nostril of a small animal, a skin contact microphone, both being connected via electrical cables to an amplifer arranged to simultaneously and selectively audibly indicate the respiratory and the cardiovascular functions of the animal to the listener. Using a cuff and gauge, systolic and diastolic blood pressure can also be monitored. This device connected the patient by an electrical line to a speaker system.

Further, the invention disclosed in U.S. Pat. No. 2,669,465, a device for indicating the cessation of cardiac function, employs a flexible tube for transmitting the heart sounds to a microphone. The present invention seeks to eliminate the danger of diminishing the acoustic strength of the heart signal caused by tubing.

BRIEF DESCRIPTION OF THE INVENTION

This is a new and improved solely patient mounted and supported constant monitoring stethoscopic and radio transmitter system with a remote radio receiver and audio means. The system is solely connected using suction and supported on the chest of a patient. The component parts may be sized and shaped for mounting and supporting the system on a patient and special feactures may be included for use on newborn babies. The system is connected to a local radio receiver only by radio waves from the system's radio transmitter antenna. The radio receiver produces amplified stethoscopic monitored sounds to attending personnel that are unconnected to the patient or said stethoscope and radio transmitter, except by radio waves. The stethoscope has an acoustic contactor body that includes an acoustic pickup recess for picking up acoustical sounds in a patient's chest. The said acoustic recess is formed by the partial vacuum created by said suction cup stethoscope head being placed on the skin of the patient. The wet skin of a newborn makes a particularly suitable surface for suction adherence and thus this invention can be employed to monitor and detect the onset of potential danger in a newborn almost as soon as the delivery is completed. Further, the suction connection provides an environment within the acoustic recess free of background noise, thus providing a pure heart and chest signal for the detection of even the slightest abnormality. A microphone is connected to the recess for converting acoustical sounds in the recess to electrical signals. The radio transmitter has a battery power source and an input connected to the microphone. The radio transmitter amplifies the electrical signal and discharges the signal to the antenna for transmitting radio waves out into the room in which the patient is present. The radio receiver receives the signal and provides an audio output in the room.

The system may be contained in a contactor body, except for the antenna. The contactor body is relatively light weight to avoid causing discomfort to the patient. The contactor body may be of such a light weight design that it may be supported solely by the chest of a newborn baby patient. The transmitter, batteries and antenna may be encapsulated to provide electrical isolation from the patient's heart [neuroanatomical system].

The instant invention can be used either with a transmitter and remote receiver, or may connect to a proper audio means via electric wire and proper universal adapter where it is undesirable to use a broadcast signal, as in an area of high radio wave interference.

During a surgical operation or delivery of babies it is customary for the anesthetist to keep a close watch on the function of the patient's heart and respiratory system and the newborns heart and respiratory system. However, the anesthetist is often kept preoccupied with other details of his or her function and precious moments may pass between the onset of emergency situations such as cardiac arrest and its discovery. This is especially pertinent when it is realized that after delivery, the physician suddenly has two patients, not one. A second suction stethoscope head can be applied to the newborn immediately to begin constant monitoring of his or her heart and breath status on a second channel when the receiver is a stereo FM receiver.

It is, therefore, a principal object of this invention to provide a stethoscope which will transmit to a remote radio receiver to provide amplified stethoscope heart and chest sounds to provide an audible warning or give an indication of cardiac functions so that proper measures may be instituted to restore the circulation of blood and, eventually, cardiac activity while the body tissues are still in good condition and before irreparable damage has been done.

It is another object of this invention to provide a lightweight improved constant monitoring suction stethoscope and radio transmitter/receiver system.

It is a further object of this invention to provide a lightweight heart and chest sound detection device which can be mounted on the patient's chest using only suction without causing discomfort, including a newborn.

It is another object of this invention to monitor the cardiorespiratory function of newborns or any patient routinely with simplicity and accuracy.

It is another object of this invention to provide a precordial chest stethoscope that can be easily mounted for use on patients in a supine, prone, lateral, sitting or any other position.

It is still a further object of this invention to provide a backup to the EKG used in telemetry units in the hospital to monitor cardiac function.

It is another object of the invention to provide a constant monitoring system adapted to pick up the heart sounds and amplify them so that they may be heard throughout the operating room, which all operating room personnel may hear.

Another object of this inventionn is to allow other sound testing systems to be connected to the transmitting portion of the present system through the transducer and a new and improved transformer.

These and other objects, features, and advantages of the invention will be readily apparent from the following descriptions when considered together with the accompanying drawings.

DETAILED DESCRIPTION OF THE PREFERRED EMBODIMENT

Figure 2A:
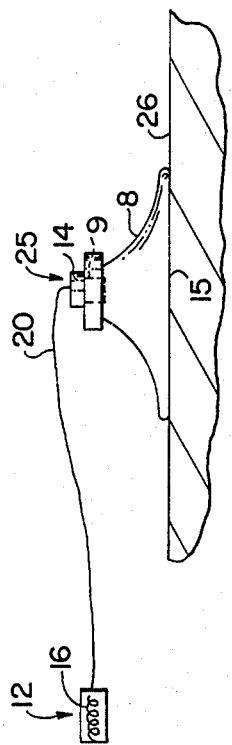
FIG. 2A is an illustration of one embodiment of the stethescope head.
Figure 2B:
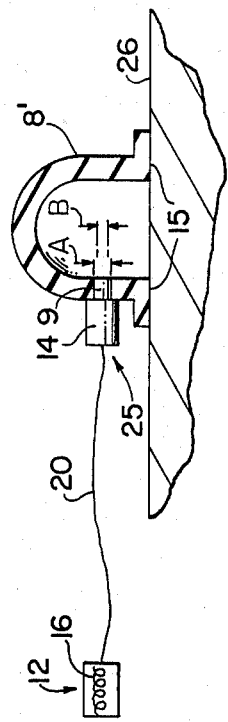
FIG. 2B is an illustration of another embodiment of a stable stethescope head.
Figure 1:
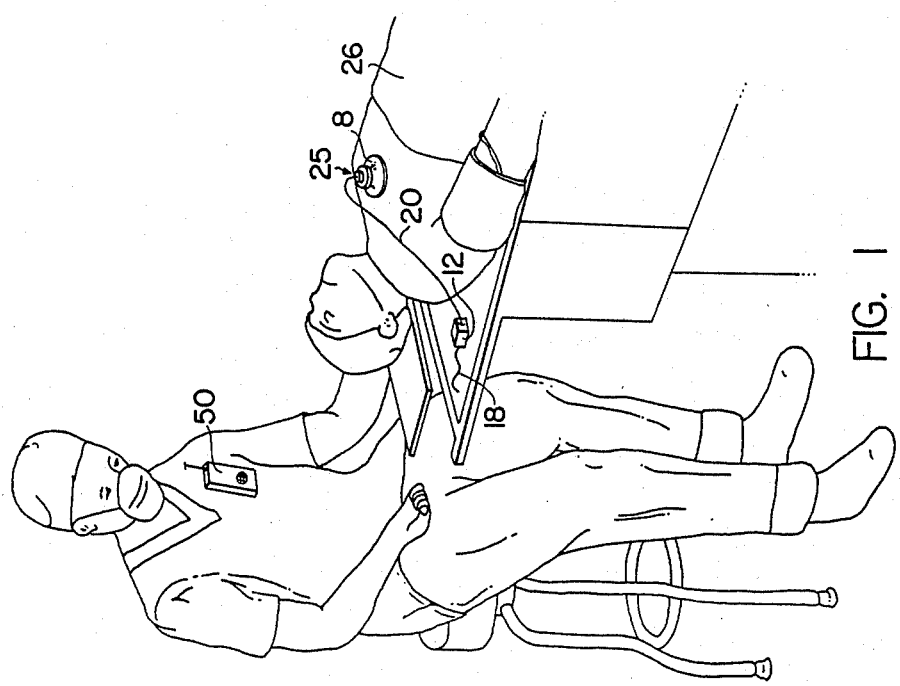
FIG. 1 is an illustration of the invention in use.
Figure 9:
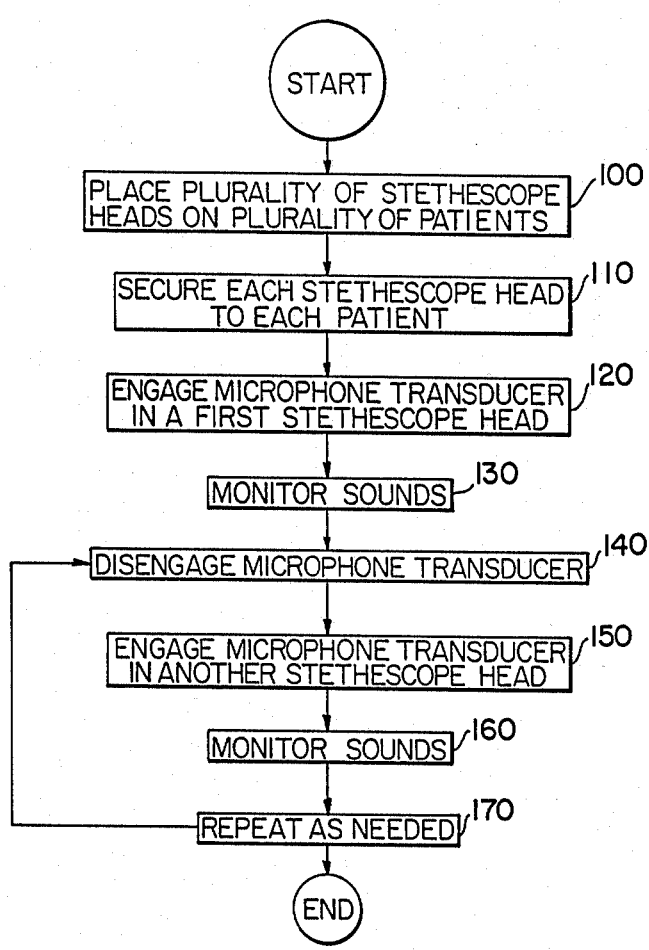
FIG. 9 is a block diagram illustrating one method of using the present invention.

Referring first to FIGS. 1 and 2A and 2B of the drawings, numerals 8 and 8' indicate a suction stethoscope head adapted to be secured to the patient by suction or by other known means such as adhesive at a point where it is desired to observe or monitor human sounds. The stethoscope head can be similar to the chest piece of an ordinary stethoscope, may be of the bell type shown as 8' in FIG. 2B or disc type shown as 8 in FIG. 2A, and can be conveniently secured to the patient by means of suction and can be solely supported thereupon. Transducer 25 forms an airtight seal with stethoscope heads 8 and 8', in FIGS. 2A and 2B. Male end 9 is larger in diameter A than opening B in the squeeaeable head 8 in FIG. 2B providing an automatic airtight seal. The stethoscope head 8 remains fixed in position on the area to be monitored of patient's body by suction alone. The body can be in any position while the system is monitoring. The connection shown in FIG. 2B is more stable than the top microphone connection shown in FIG. 2A. Suction stethoscope heads 8 and 8' are of a flexible material which will yield to fingertip pressure without distoring or vitiating the airtight seal between heads 8, 8' and microphone 14. FIGS. 2A and 2B show two possible embodiments of stethescope heads 8, 8' which commonly utilize the same transducer 25. Thus, it is apparent that a single transducer assembly means could commonly service a number of such heads which are by themselves mounted on individual patients whereby the attending personnel simply engages and subsequently disengages the transducer assembly from different heads. FIG. 9 illustrates the method of servicing a plurality of patients. The steps 100 through 140 illustrate that one of a number of heads secured to an equal number of patients may be connected to the transducer for monitoring. Steps 140 through 170 illustrate that additional different heads may be alternatively connected with the transducer as is required by each patient's needs. The patient contact surface 15 is essentially circular. The body of said stethoscope heads 8, 8' are symmetrical about an axis concentric with said patient contact surface 15. When it is necessary or convenient to monitor remotely or in any way unconnected to the patient, suction heads 8, 8' are arranged in contact with the area to be monitored on the body of the patient about patient contact surface 15, as shown in FIGS. 2A, 2B. An appropriate magnitude of pressure is applied using fingers to the outer surface of head 8, 8' causing the body of head 8 to yield inwardly toward the patient 26, thereby decreasing the volume of the acoustic recess within head 8, 8' and forcing an equal volume of air out of the acoustic recess between patient contact surface 15 and the patient's skin. When the applied pressure is held constant, as when the person applying the system is about to let go, no more air is forced out. As the head 8, 8' is released, its body attempts to return to its equilibrium shape, thereby drawing some outside air back in. More importantly, the suction action draws patient's skin toward and into firm contact with patient contact surface 15. Once a seal is made about surface 15, the head 8 will remain in place. The wet skin of a newborn provides an excellent surface for suction contact.

Figure 4:
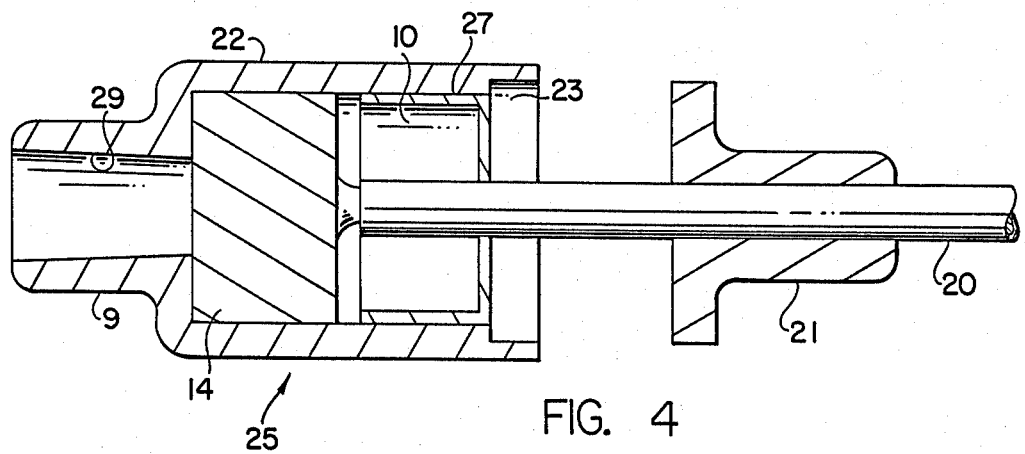
FIG. 4 is a side view of the transducer (an electrtret microphone) housing in cross section for the vacuum stethescope.

The acoustic heart and chest sounds detected in the acoustic recess of stethoscope head 8, 8' are communicated by sound pressure waves into a transducer, referred to generally by reference numeral 25 in FIG. 4. Transducer housing 22 provides a vacuum airtight seal around vacuum chamber 10. A vacuum seal precludes background noise from combining with and distorting or diminishing the monitoring signal. Said vacuum airtight seal is accomplished by fitting a microphone element 14 against the inside surface of transducer housing 22 closing off opening 29 in input male connector end 9 as seen in FIG. 4. At the other end, transducer housing end piece 21 is brought into contact with transducer end opening 23 and sealed, using any appropriate sealing method, against transducer housing 22. Two wire cable 20 is also in airtight contact through transducer housing end piece 21 and wired to electret microphone element 14. In the preferred embodiment, microphone 14 is an Archer PC mount electret microphone Catalog No.

Figure 3A:
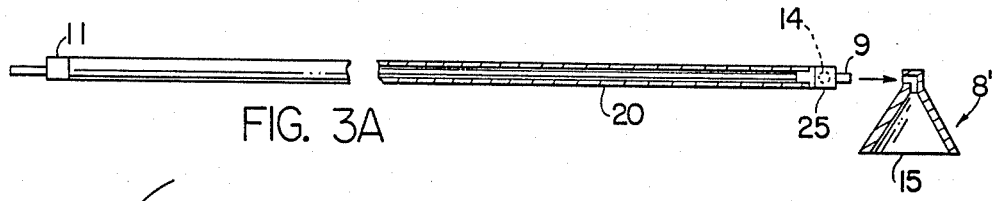
FIG. 3A is a side view in cross section of the stethescope, microphone, wires and jack.
Figure 3B:
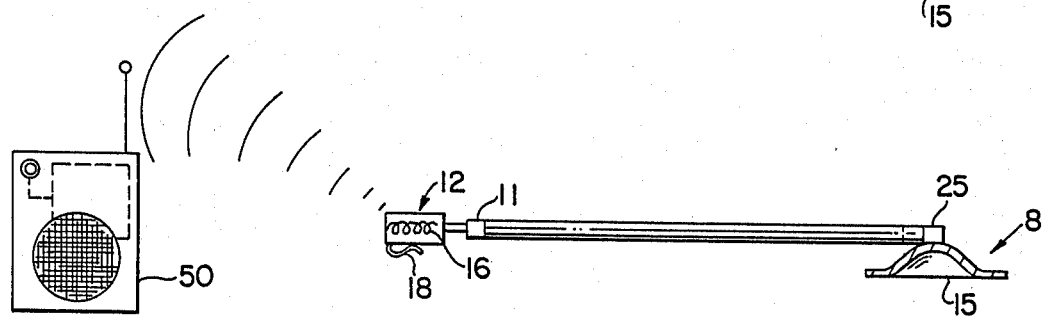
FIG. 3B is a side view of the stethescope, microphone, wires, transducer, antenna and receiver.
Figure 8:
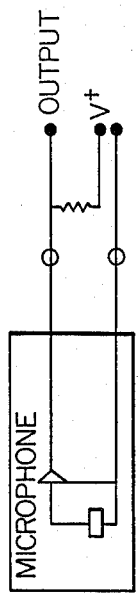
FIG. 8 is a schematic of the microphone element.

270-090 with an operating voltage of 2.0 to 10 VDC, 4.5 VDC optimum, 1.0 mAmps maximum, 4.0 dB minimum signal to noise radio, −6.5 to +4.0 dB sensitivity, and an output impedence of 1.0 KOhm. A schematic illustration of such a microphone element appears in FIG. 8. Plug 11, as shown in FIGS. 3A and 3B, at outer end of cable 20 communicates the stethescope head 8 through transducer 25 to transmitter 16 and thusly to attending medical personnel. Additionally, a metal shield 27, as shown in FIG. 4 may be placed in the transducer housing 22 to limit outside electronic interference with the output signal of microphone 14.

The radio transmission means, indicated by reference numeral 12 includes a transmitter 16 connected to an outwardly extending antenna 18. The antenna may be in line 20 or the antenna may be one of the wires in the lines 20. Microphone 14, when connected to stethescope head 8, may convert the chest sounds into electrical impulses which are transmitted via leads 20 to transmitter 16. The microphone may be a condenser type. A suitable battery power source, now shown, may be used to supply the electronic transmitter 16 with the voltage necessary to transmit the detected and amplified impulses from the microphone 14 to a remote radio wave receiver 50, as in FIG. 3B. Radio wave transmission means can be associated nearby the patient using a clip-on feature, not shown, or any other suitable means of locating said unit 12.

In an alternative embodiment of the invention, two separate stethescope heads can be used, as with a mother and her newborn. Any number of stetescope heads can be used on one or more patients. For instance, both the heart and chest sounds and blood pressure pulse of a single patient can be monitored simultaneously.

Figure 6A:
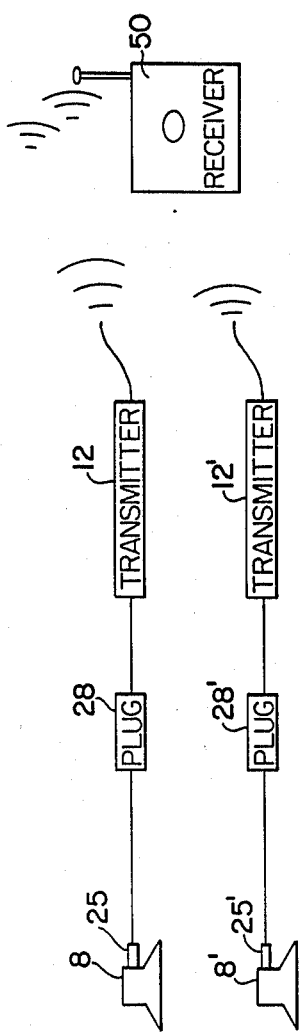
FIGS. 6A and 6B are illustrations of two embodiments invention showing multiple stethoscopes transmitting via transmitters to a single receiving device for audible patient monitoring.
Figure 6B:
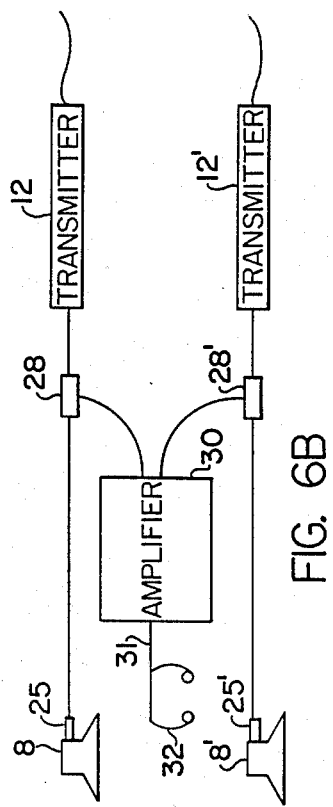

In FIGS. 6A, 6B are depicted two separate stethoscope heads 8 and 8' which connect to their respective transducers 25 and 25'. The electronic signal produced therefrom is transmitted via cables 20 and 20' to juncture plugs 28 and 28'. From there said signal can be diverted either simultaneously or exclusively to dual channel amplifier as shown in FIG. 6B or to transmitters 12 and 12' for relay either through leads 31 to earphones 32 or to remote receiver 50, respectively. The embodiment of FIG. 6B provides a convenient means of monitoring a patient in areas of high radio wave interference.

Figure 5:
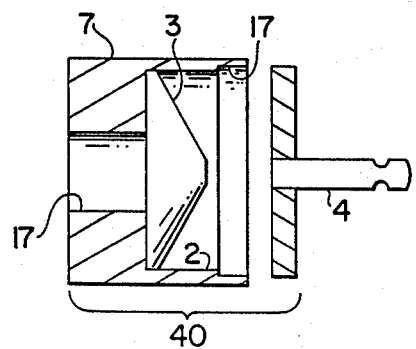
FIG. 5 is a transfomer for audio output speakers.
Figure 7:
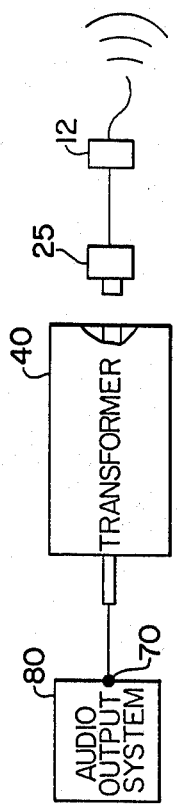
FIG. 7 is a block diagram of various systems showing the various connections that can be made to transmit audio waves to a receiver inexpensively.

The transformer, i.e. means to transform input from an electronic source to form acoustic vibrations, 40 of FIG. 5 includes transformer housing 7 with an opening 17 sized to accomodate input male connector end 9 of transducer 25. Plug 4, which can be a miniature phone plug, relays heart and chest sounds from a heart and chest sound source, as in an ultrasonic stethoscope comprising an output jack as depicted by FIG. 7 element 70, which can be the audio output system 80 of FIG. 7, to a small speaker 3. Speaker 3 converts the electronic heart and chest sound signal to acoustic vibrations. When speaker 3 is positioned inside transformer housing recess 2, said acoustic vibrations can be picked up by microphone 14 of transducer 25 connected into transformer housing opening 17. The acoustic vibrations are then converted into an electric signal by microphone 14 and can be communicated to attending personnel by any of the means discussed in this specification. Such an embodiment is needed when, for example, a stethoscopic monitoring means is used which cannot directly articulate with transducer 25. Thus, the present invention can be used with any type of heart, chest, blood pressure, or any other sound detection and monitoring means.

The amplifier 30 may be a Sharp FM Stereo Preset Receiver, FDDIC:ATF90ITF0029.

The jack 11 may be an RCA jack with the ground lead of the microphone 14 and the transmitter isolated from one another.

Supervisor can monitor two or more assistants with the present invention. The invention allows the supervising anesthesiologist continuous monitoring and to have available continuous updating information when not in physical contact with the patient or physically close to the supervisor.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A constant monitoring stethoscope and radio wave transmitter and receiver system connectable to a local radio receiver only by radio waves for amplifying stethoscopically monitored heart and chest sounds to attending personnel that are not directly connected to the patient or said stethoscope and transmitter system, said constant monitoring stethoscope and radio wave transmitter and receiver system comprising:

a stethoscope head defining an acoustic contactor body means having a closable opening formed therein including an acoustic pickup recess means for capturing acoustical vibrations between the skin of the patient and the acoustic contactor body means, a microphone transducer means sealably connected directly into said opening formed in said connector body to enclose and seal said contactor body and define a sealed acoustic pickup recess means for converting acoustical vibrations in said recess to electrical signals;

a radio transmitter means having an input means, said input means connected to said transducer microphone, said input means of said radio transmitter means for receiving said electrical signals, said radio transmitter means including amplifier means connected to said input means for amplifying said electrical signals, and an antenna means connected to said radio transmitter means to transmit radio waves of said acoustical sounds, said contactor body means connecting said constant monitoring stethoscope and radio wave transmitter system to a patient, said contactor body means formed from a flexible material and shaped as an inverted concave member forming in said recess a partial vacuum acoustical space between the patient's skin and said recess means wherein acoustic vibrations permeating from the patient's inner organs are transferred without distortion or being diminished through said partial vacuum in said acoustical space to said sealably connected microphone transducer means and then transmitted to the local radio receiver.

2. A constant monitoring suction stethoscope and radio transmitter and receiver system as set forth in claim 1, wherein:

said contactor body means has a suction cup contact portion means formed from said flexible material and surrounds said recess means, said suction cup contact portion means enabling quick mounting and connecting of said system to a patient, especially a newborn, and for quickly removing said contactor body means for placement at another location on the patient, and wherein said contactor body means is configural.

3. A constant monitoring stethoscope and radio wave transmitter and receiver system as set forth in claim 2, wherein:

said contactor body means closable opening is a side opening for receiving said transducer microphone means, said transducer microphone means includes a housing which provides a vacuum, air tight seal, around a portion of said transducer microphone means and has a connector end for mating and sealing in said side opening of said body, said opening being of smaller size than said connector end thus maintaining said suction cup's ability to connect to the patient.

4. A constant monitoring stethoscope and radio wave transmitter and reciever system as set forth in claim 3, wherein:

the system further comprises a transformer means having an input and an output and comprises an audio output device, said housing has an inside diameter dampening structure and said connector end is connected to said transformer means output, said transformer means input includes a jack for connection to said audio output device to transfer the output by radio waves to a receiver.

5. A constant monitoring suction stethoscope and radio transmitter and receiver system as set forth in claim 1 wherein said contactor body means further includes an adhesive whereby said contactor body means of said stethoscope head is attached to the skin of the patient by said adhesive.

6. A process for utilizing a stethoscope constant monitoring system including a stethoscope head defining an acoustic contactor body means having a closable opening formed therein including an acoustic pickup recess means for capturing acoustical vibrations between the skin of the patient and the acoustical contactor body means, a microphone transducer means sealably connected directly into the said opening formed in said connector body to enclose and seal said contactor body and define a sealed acoustic pickup recess means for converting acoustical vibrations in said recess to electrical signals, said contactor body means formed from a flexible material and shaped as an inverted concabe member which when squeezed by fingertip pressure of the attending personnel forming in said recess a partial vacuum acoustical space between the patient's skin and said recess means wherein acoustic vibrations permeating from the patient's inner organs are transferred without distortion or being diminished through said partial vacuum in said acoustical space to said sealably connected microphone transducer means comprising the steps of:

(a) selecting the desired location on a patient to be monitored by said stethoscope constant monitoring system, (b) arranging said suction stethoscope head upon said area, (c) applying the necessary pressure upon said suction stethoscope head so as to cause the body of said suction stethoscope head to yield inwardly toward the patient's body thereby forcing a volume of air within the acoustical recess to emerge from said recess passing through the area of contact between said patient's body and said suction stethoscope head; and (d) disengaging all pressure and fully removing the pressure (hand) source from said suction stethoscope head thereby causing a partial outward displacement of the inwardly displaced portion of said suction stethoscope head which will result in a state of negative pressure relative to ambient pressure within the acoustic recess of said suction stethoscope head and causing said suction stethoscope head to come into firm contact with said patient, said pressure differential resulting in the continuous equilibrium fixed position of said suction stethoscope head.

7. A process for utilizing a stethoscope constant monitoring system including a solely patient mounted heart and breath sound detection means comprising a cup with an acoustical recess designed and arranged to remain connected in any desired location on a patient for monitoring acoustical vibrations therefrom and a detachable microphone transducer means sealably yet removably connectable to the cup, comprising the steps of:

(a) selecting the desired location on a plurality of patients to be monitored by said stethoscope constant monitoring system, (b) providing a plurality of said cups;

(c) arranging each of said cups upon said locations;

(d) securing said plurality of said cups to the bodies of the patients; and (e) engaging said microphone transducer means in a first of said plurality of said cups to monitor heart and breath sounds;

(f) quickly disengaging said microphone transducer means from said first cup and reconnecting it to another different cup of said plurality of said cups.

* * * * *